US008500732B2

(12) United States Patent  (10) Patent No.: US 8,500,732 B2
Truckai et al.  (45) Date of Patent: *Aug. 6, 2013

(54) ENDOMETRIAL ABLATION DEVICES AND SYSTEMS

(75) Inventors: Csaba Truckai, Saratoga, CA (US); Akos Toth, Tata (HU)

(73) Assignee: Hermes Innovations LLC, Cupertino, CA (US)

( * ) Notice: Subject to any disclaimer, the term of this patent is extended or adjusted under 35 U.S.C. 154(b) by 725 days.

This patent is subject to a terminal disclaimer.

(21) Appl. No.: 12/605,546

(22) Filed: Oct. 26, 2009

(65) Prior Publication Data

US 2010/0114089 A1   May 6, 2010

Related U.S. Application Data

(63) Continuation-in-part of application No. 12/541,043, filed on Aug. 13, 2009, now Pat. No. 8,372,068, and a continuation-in-part of application No. 12/541,050, filed on Aug. 13, 2009, now Pat. No. 8,382,753.

(60) Provisional application No. 61/196,870, filed on Oct. 21, 2008.

(51) Int. Cl.
    *A61B 18/18* (2006.01)
(52) U.S. Cl.
    USPC .............................................. 606/41; 606/45
(58) Field of Classification Search
    USPC ................ 606/41–45; 600/372–397
    See application file for complete search history.

(56) References Cited

U.S. PATENT DOCUMENTS

| 4,949,718 A | 8/1990 | Neuwirth et al. |
| 4,979,948 A | 12/1990 | Geddes et al. |
| 5,045,056 A | 9/1991 | Behl |
| 5,078,717 A | 1/1992 | Parins |
| 5,084,044 A | 1/1992 | Quint |

(Continued)

FOREIGN PATENT DOCUMENTS

| EP | 1 236 440 A1 | 9/2002 |
| WO | WO 2005/122938 A1 | 12/2005 |
| WO | WO 2011/053599 A1 | 5/2011 |

OTHER PUBLICATIONS

U.S. Appl. No. 12/944,466, filed Nov. 11, 2010, Toth et al.

(Continued)

*Primary Examiner* — Linda Dvorak
*Assistant Examiner* — Amanda Scott
(74) *Attorney, Agent, or Firm* — Wilson, Sonsini, Goodrich & Rosati

(57) ABSTRACT

Systems and methods for endometrial ablation. The systems include a handle and elongated introducer sleeve extending to an expandable working end having a fluid-tight interior chamber. A thin dielectric wall surrounds at least a portion of the interior chamber and has an external surface for contacting endometrial tissue. The thin dielectric wall surrounds a collapsible-expandable frame and receives an electrically non-conductive gas. First and second polarity electrodes are exposed to the interior and exterior of the chamber, respectively. A radiofrequency power source operatively connects to the electrode arrangement to apply a radiofrequency voltage across the first and second electrodes, wherein the voltage is sufficient to initiate ionization of the neutral gas into a conductive plasma within the interior chamber, and to capacitively couple the current in the plasma across the thin dielectric wall to ablate endometrial tissue engaged by the external surface of the dielectric structure.

40 Claims, 13 Drawing Sheets

U.S. PATENT DOCUMENTS

| | | |
|---|---|---|
| 5,191,883 A | 3/1993 | Lennox et al. |
| 5,242,390 A | 9/1993 | Goldrath |
| 5,248,312 A | 9/1993 | Langberg |
| 5,277,201 A | 1/1994 | Stern |
| 5,344,435 A * | 9/1994 | Turner et al. ............... 607/101 |
| 5,374,261 A | 12/1994 | Yoon |
| 5,401,272 A | 3/1995 | Perkins |
| 5,441,498 A | 8/1995 | Perkins |
| 5,443,470 A | 8/1995 | Stern et al. |
| 5,501,681 A | 3/1996 | Neuwirth et al. |
| 5,505,730 A | 4/1996 | Edwards |
| 5,558,672 A | 9/1996 | Edwards |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | LaFontaine et al. |
| 5,653,692 A | 8/1997 | Masterson et al. |
| 5,681,308 A | 10/1997 | Edwards et al. |
| 5,697,281 A | 12/1997 | Eggers |
| 5,697,882 A | 12/1997 | Eggers |
| 5,713,942 A | 2/1998 | Stern et al. |
| 5,769,846 A | 6/1998 | Edwards et al. |
| 5,769,880 A | 6/1998 | Truckai et al. |
| 5,800,493 A | 9/1998 | Stevens et al. |
| 5,827,273 A | 10/1998 | Edwards |
| 5,843,020 A | 12/1998 | Tu et al. |
| 5,846,239 A | 12/1998 | Swanson et al. |
| 5,860,974 A | 1/1999 | Abele |
| 5,876,340 A | 3/1999 | Tu et al. |
| 5,891,094 A | 4/1999 | Masterson et al. |
| 5,891,134 A | 4/1999 | Goble et al. |
| 5,891,136 A | 4/1999 | McGee |
| 5,902,251 A | 5/1999 | vanHooydonk |
| 5,904,651 A | 5/1999 | Swanson et al. |
| 5,925,038 A * | 7/1999 | Panescu et al. ............... 606/41 |
| 5,954,714 A | 9/1999 | Saadat et al. |
| 5,964,755 A | 10/1999 | Edwards |
| 5,976,129 A | 11/1999 | Desai |
| 5,997,534 A | 12/1999 | Tu et al. |
| 6,024,743 A | 2/2000 | Edwards |
| 6,026,331 A | 2/2000 | Feldberg et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,113,597 A | 9/2000 | Eggers |
| 6,139,570 A | 10/2000 | Saadat et al. |
| 6,146,378 A | 11/2000 | Mikus et al. |
| 6,149,620 A | 11/2000 | Baker et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallsten et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,508,815 B1 | 1/2003 | Strul et al. |
| 6,551,310 B1 | 4/2003 | Ganz et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | VanDusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,923,805 B1 | 8/2005 | LaFontaine et al. |
| 6,929,642 B2 | 8/2005 | Xiao et al. |
| 6,949,096 B2 | 9/2005 | Davison et al. |
| 6,951,569 B2 | 10/2005 | Nohilly et al. |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fijield et al. |
| 7,087,052 B2 | 8/2006 | Sampson et al. |
| 7,118,590 B1 | 10/2006 | Cronin |
| 7,179,255 B2 | 2/2007 | Lettice et al. |
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,294,126 B2 | 11/2007 | Sampson et al. |
| 7,297,143 B2 | 11/2007 | Woloszko et al. |
| 7,326,201 B2 | 2/2008 | Fijield et al. |
| 7,331,957 B2 | 2/2008 | Woloszko et al. |
| RE40,156 E | 3/2008 | Sharps et al. |
| 7,371,231 B2 | 5/2008 | Rioux et al. |
| 7,371,235 B2 | 5/2008 | Thompson et al. |
| 7,381,208 B2 | 6/2008 | van der Walt et al. |
| 7,387,628 B1 | 6/2008 | Behl et al. |
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van Wyk et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,749,159 B2 | 7/2010 | Crowley et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 * | 7/2011 | Felts et al. ............... 600/573 |
| 8,197,476 B2 | 6/2012 | Truckai |
| 8,197,477 B2 | 6/2012 | Truckai |
| 2002/0022870 A1 * | 2/2002 | Truckai et al. ............... 607/101 |
| 2002/0068934 A1 | 6/2002 | Edwards et al. |
| 2002/0082635 A1 | 6/2002 | Kammerer et al. |
| 2003/0130655 A1 | 7/2003 | Woloszko et al. |
| 2003/0153905 A1 | 8/2003 | Edwards et al. |
| 2003/0171743 A1 | 9/2003 | Tasto et al. |
| 2003/0208200 A1 | 11/2003 | Palanker et al. |
| 2004/0002702 A1 | 1/2004 | Xiao et al. |
| 2004/0087936 A1 | 5/2004 | Stern et al. |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0165389 A1 | 7/2005 | Swain et al. |
| 2005/0182397 A1 | 8/2005 | Ryan |
| 2005/0192652 A1 | 9/2005 | Cioanta et al. |
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0089637 A1 | 4/2006 | Werneth et al. |
| 2006/0189971 A1 | 8/2006 | Tasto et al. |

| | | | | | | |
|---|---|---|---|---|---|---|
| 2006/0189976 | A1 | 8/2006 | Karni et al. | 2010/0049190 A1 | 2/2010 | Long et al. |
| 2006/0224154 | A1 | 10/2006 | Shadduck et al. | 2010/0100091 A1 | 4/2010 | Truckai et al. |
| 2006/0259025 | A1 | 11/2006 | Dahla | 2010/0100094 A1 | 4/2010 | Truckai et al. |
| 2007/0021743 | A1 | 1/2007 | Rioux et al. | 2010/0106152 A1 | 4/2010 | Truckai et al. |
| 2007/0083192 | A1 | 4/2007 | Welch | 2010/0121319 A1 | 5/2010 | Chu et al. |
| 2007/0161981 | A1 | 7/2007 | Sanders et al. | 2010/0125269 A1 | 5/2010 | Emmons et al. |
| 2007/0213704 | A1 | 9/2007 | Truckai et al. | 2010/0137855 A1 | 6/2010 | Berjano Zanon et al. |
| 2007/0282323 | A1 | 12/2007 | Woloszko et al. | 2010/0137857 A1 | 6/2010 | Shroff et al. |
| 2007/0287996 | A1 | 12/2007 | Rioux | 2010/0152725 A1 | 6/2010 | Pearson et al. |
| 2007/0288075 | A1 | 12/2007 | Dowlatshahi | 2010/0185191 A1 | 7/2010 | Carr et al. |
| 2007/0293853 | A1 | 12/2007 | Truckai et al. | 2010/0198214 A1 | 8/2010 | Layton et al. |
| 2008/0058797 | A1 | 3/2008 | Rioux | 2010/0204688 A1 | 8/2010 | Hoey et al. |
| 2008/0097425 | A1* | 4/2008 | Truckai ............... 606/41 | 2010/0217256 A1 | 8/2010 | Strul et al. |
| 2008/0125765 | A1 | 5/2008 | Berenshteyn et al. | 2010/0228239 A1 | 9/2010 | Freed |
| 2008/0125770 | A1 | 5/2008 | Kleyman | 2010/0228245 A1 | 9/2010 | Sampson et al. |
| 2008/0154238 | A1 | 6/2008 | McGuckin | 2010/0286680 A1 | 11/2010 | Kleyman et al. |
| 2008/0208189 | A1* | 8/2008 | Van Wyk et al. ............ 606/42 | 2011/0004205 A1 | 1/2011 | Chu et al. |
| 2008/0221567 | A1 | 9/2008 | Sixto, Jr. | 2011/0060391 A1 | 3/2011 | Unetich et al. |
| 2008/0249518 | A1 | 10/2008 | Warnking et al. | 2011/0112524 A1 | 5/2011 | Stern et al. |
| 2009/0048593 | A1 | 2/2009 | Ganz et al. | 2012/0116384 A1 | 5/2012 | Truckai |
| 2009/0054888 | A1 | 2/2009 | Cronin | 2012/0130361 A1 | 5/2012 | Toth et al. |
| 2009/0054892 | A1 | 2/2009 | Rioux et al. | | | |
| 2009/0076494 | A1 | 3/2009 | Azure | | | |
| 2009/0105703 | A1 | 4/2009 | Shadduck | | | |
| 2009/0131927 | A1 | 5/2009 | Kastelein et al. | | | |
| 2009/0149846 | A1 | 6/2009 | Hoey et al. | | | |
| 2009/0163908 | A1 | 6/2009 | MacLean et al. | | | |
| 2009/0209956 | A1 | 8/2009 | Marion | | | |
| 2009/0306654 | A1 | 12/2009 | Garbagnati | | | |
| 2010/0004595 | A1 | 1/2010 | Nguyen et al. | | | |
| 2010/0036372 | A1 | 2/2010 | Truckai et al. | | | |
| 2010/0042095 | A1 | 2/2010 | Bigley et al. | | | |
| 2010/0042097 | A1 | 2/2010 | Newton et al. | | | |

OTHER PUBLICATIONS

International search report and written opinion dated Feb. 2, 2011 for PCT/US2010/056591.

International search report and written opinion dated Dec. 10, 2009 for PCT/US2009/060703.

International search report and written opinion dated Dec. 14, 2010 for PCT/US2010/054150.

* cited by examiner

ENDOMETRIAL ABLATION DEVICES AND SYSTEMS

REFERENCE TO RELATED APPLICATIONS

This application is a continuation in part of U.S. application Ser. No. 12/541,043; filed Aug. 13, 2009 and U.S. application Ser. No. 12/541,050 both filed on Aug. 13, 2009, which both claim the benefit of provisional Application No. 61/196,870, filed on Oct. 21, 2008, the full disclosures of which are incorporated herein by reference.

BACKGROUND

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-wall dielectric member enclosing an ionized gas.

A variety of devices have been developed or proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. No. 6,736,811 and U.S. Pat. No. 5,925,038 show an inflatable conductive electrode.

BRIEF SUMMARY

The present invention provides a systems and methods for endometrial ablation, which relate to method and apparatus disclosed in U.S. application Ser. No. 12/541,043; filed Aug. 13, 2009 and U.S. application Ser. No. 12/541,050 both filed on Aug. 13, 2009, the full disclosures of which are incorporated herein by reference. The systems for delivering radiofrequency current to tissue comprises a handle and elongated introducer sleeve extending to an expandable working end having a fluid-tight interior chamber. A thin dielectric wall surrounds at least a portion of the interior chamber and has an external surface for contacting endometrial tissue. The thin dielectric wall surrounds a collapsible-expandable frame. A gas inflow lumen and a gas outflow lumen are provided to communicate with the interior chamber for delivering a flow of an electrically non-conductive gas into and through the chamber. A first polarity electrode is provided which has a surface exposed to the interior chamber. A second polarity electrode exterior of the interior chamber is also provided that includes a surface adapted to contact body tissue. The system further includes a radiofrequency power source operatively connected to the electrode arrangement to apply a radiofrequency voltage across the first and second electrodes, wherein the voltage is sufficient to initiate ionization of the neutral gas into a conductive plasma within the interior chamber. The voltage further is sufficient to capacitively couple the current in the plasma across the thin dielectric wall and into endometrial tissue engaged by the external surface of the dielectric structure. The treatment method generally comprises delivering a radiofrequency current to endometrial tissue in order to heat and usually ablate the tissue to a desired depth, ranging from about 2 to 6 mm.

In one embodiment, the thin dielectric wall can comprise a conformable material, typically a silicone. A conformable dielectric wall can have a thickness in the range from about 0.005" to 0.020", usually from 0.008" to 0.010". The conformable wall may be non-distensible or may be elastic so that the wall structure may be expanded. For either non-distensible or elastic dielectric walls, the device may further comprise a frame which supports the conformable material, usually where the frame can be expanded and contracted to open and close the dielectric wall.

The hand-held device of the invention typically comprises a probe with an elongated introducer sleeve and a handle for actuating the collapsible-expandable frame to expand the thin dielectric wall in a uterine cavity. The introducer sleeve typically has a bore therein to house the thin-wall dielectric structure as the sleeve is introduced into the uterine cavity. The system further includes a controller for controlling the circulation of gas in a continuous flow through the interior chamber.

The radiofrequency power source is of the type used in electrosurgery, and will typically be configured to deliver a voltage in the range from 500V (rms) to 2500V (rms), usually from 600V (rms) to 1200V (rms), typically at a current in the range from 0.1 A to 1 A, typically from 0.2 A to 0.5 A, and at a frequency in the range from 450 kHz to 550 kHz, usually from 480 kHz to 500 kHz.

The electrically non-conductive gas that is provided in a gas flow through the interior chamber can be provided from a disposable compressed gas cartridge. The flow rate of a non-conductive gas, such as argon, will typically be in the range from about 5 ml/sec to 50 ml/sec, preferably from 10 ml/sec to 30 ml/sec.

In an embodiment, a system for endometrial ablation is provided, comprising a thin dielectric wall at least partially surrounding an interior chamber and having a shape for positioning in a uterine cavity; a gas source configured to deliver a non-conductive gas into the interior chamber; a first polarity electrode exposed to the interior chamber; a second polarity electrode external to the interior chamber for contacting patient tissue; and a radiofrequency energy source coupled to the first and second polarity electrodes for providing a voltage sufficient to convert the non-conductive gas to a plasma and to capacitively couple current across the dielectric wall to endometrial tissue.

The dielectric wall may have a triangular configuration for contacting endometrial tissue about the uterine cavity. The dielectric wall may comprise a distensible material or a non-distensible material, and may be formed, for example, from silicone.

In embodiments, the dielectric wall has a thickness in the range from 0.005 inches to 0.020 inches. The dielectric wall may be capable of contracted and expanded shapes.

A support structure may be provided in the interior chamber that is capable of contracted and expanded shapes. The support structure may include spring elements to bias the dielectric wall toward an expanded shape. The first polarity electrode may comprise at least a portion of the support structure.

An elongated introducer can be connected to the dielectric wall and support structure. The second polarity electrode can be carried by the introducer. In other embodiments, the second polarity electrode can be carried on an exterior surface of the dielectric wall.

The introducer may include at least two lumens in the introducer communicating with the interior chamber for providing a gas inflow from the gas source and a gas outflow out of the interior chamber, respectively. The gas source can comprise a remote gas source coupled to one of the two lumens in the introducer for providing the gas inflow into the interior chamber. A controller can be operatively coupled to the gas source for controlling gas inflow. The gas source can comprise a gas source coupled to one of the two lumens in the introducer for providing a gas inflow into the interior chamber. A controller can be operatively coupled to the vacuum source for controlling gas outflow.

In embodiments, the interior chamber has a volume in the range from 1 ml to 10 ml. The radiofrequency energy source is, for example, configured to deliver in the range from 500V to 2500V.

In embodiments, an endometrial ablation device is provided comprising an elongated introducer having a handle end and a working end; an expandable dielectric wall carried at the working end, defining an interior chamber, and configured, when expanded, to contact endometrial tissue; a gas source for flowing a neutral gas into the interior chamber; and first and second polarity electrodes disposed internal and external to the interior chamber, respectively. When the dielectric wall is expanded to contact endometrial tissue, application of a radiofrequency voltage across the first and second polarity electrodes when a neutral gas is within the interior chamber causes a plasma to form and capacitively couple current across the dielectric wall to ablate endometrial tissue.

In embodiments, the first polarity electrode comprises a portion of a support structure for supporting the dielectric wall in an expanded shape. The second polarity electrode may comprise an exterior surface portion of the dielectric wall, or a portion of the introducer, as examples.

The gas source may be configured to circulate gas through the interior chamber, or configured to provide a flow of neutral gas into the interior chamber, as examples.

A flow rate of the neutral gas into the interior chamber may be within the range from 0.05 ml/sec to 50 ml/sec. The gas source is configured to permit the flow of at least one of the neutral gas and the plasma out of the interior chamber.

The device may include an expandable frame for expanding the dielectric wall. In embodiments, the frame supports the dielectric wall. The expandable frame comprises the first polarity electrode.

The second polarity electrode can be carried on an exterior surface of the dielectric wall. The dielectric wall may have, for example, a triangular configuration for contacting endometrial tissue about the uterine cavity. The dielectric wall may comprises a distensible material or a non-distensible material. The dielectric wall comprises, for example, a silicone.

The dielectric wall may, for example, a thickness in the range from 0.005 inches to 0.020 inches. The dielectric wall may be capable of contracted and expanded shapes. An expandable member may be mounted to the introducer for sealing the cervical canal of the patient. The expandable member may comprise a balloon.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION

In general, an electrosurgical ablation system is described herein that comprises an elongated introducer member for accessing a patient's uterine cavity with a working end that deploys an expandable thin-wall dielectric structure containing an electrically non-conductive gas as a dielectric. In one embodiment, an interior chamber of the thin-wall dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-wall dielectric structure and the engaged tissue reaches a threshold that causes capacitive coupling across the thin-wall dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma", "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
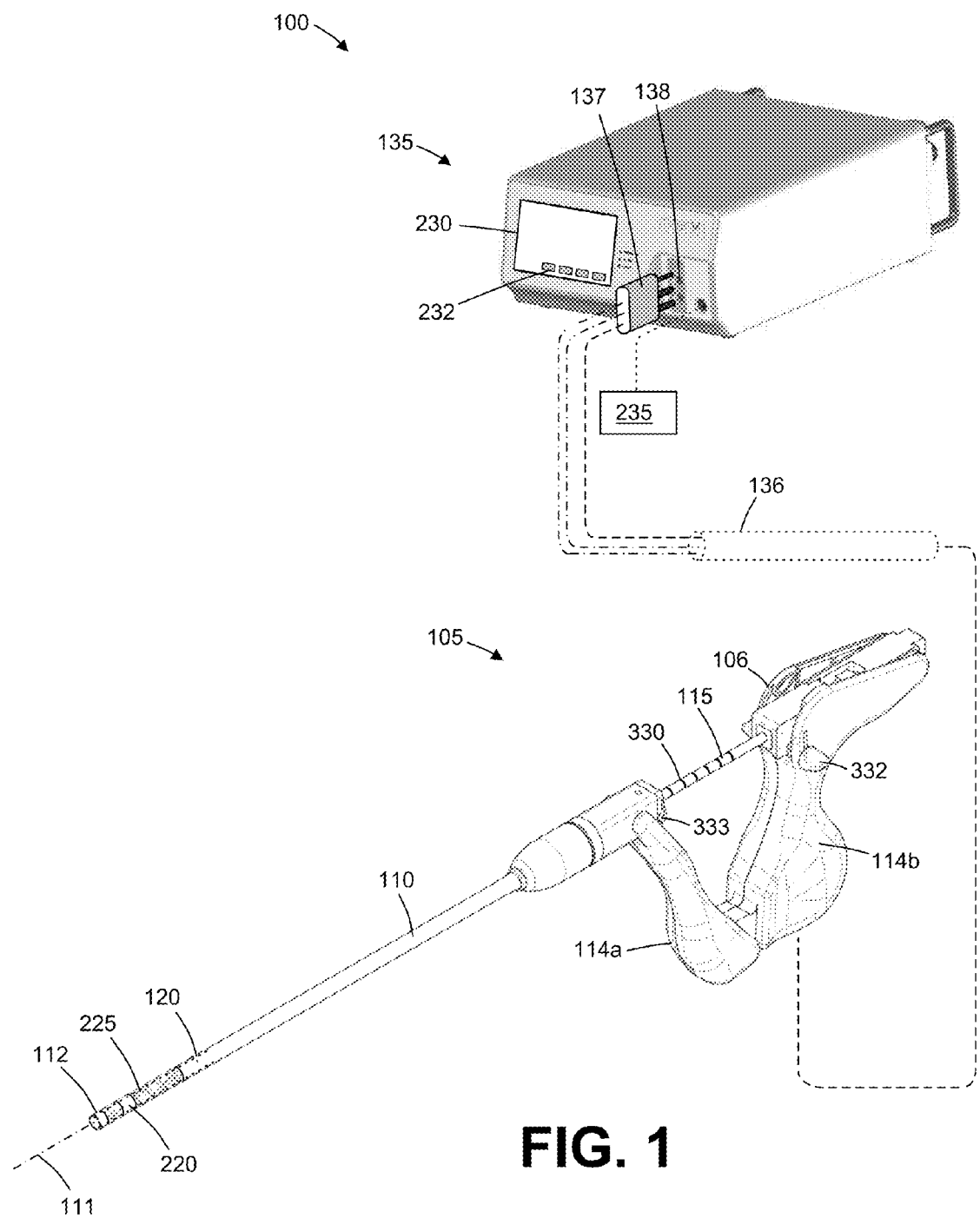
FIG. 1 is a perspective view of an ablation system corresponding to the invention, including a hand-held electrosurgical device for endometrial ablation, RF power source, gas source and controller.
Figure 2:
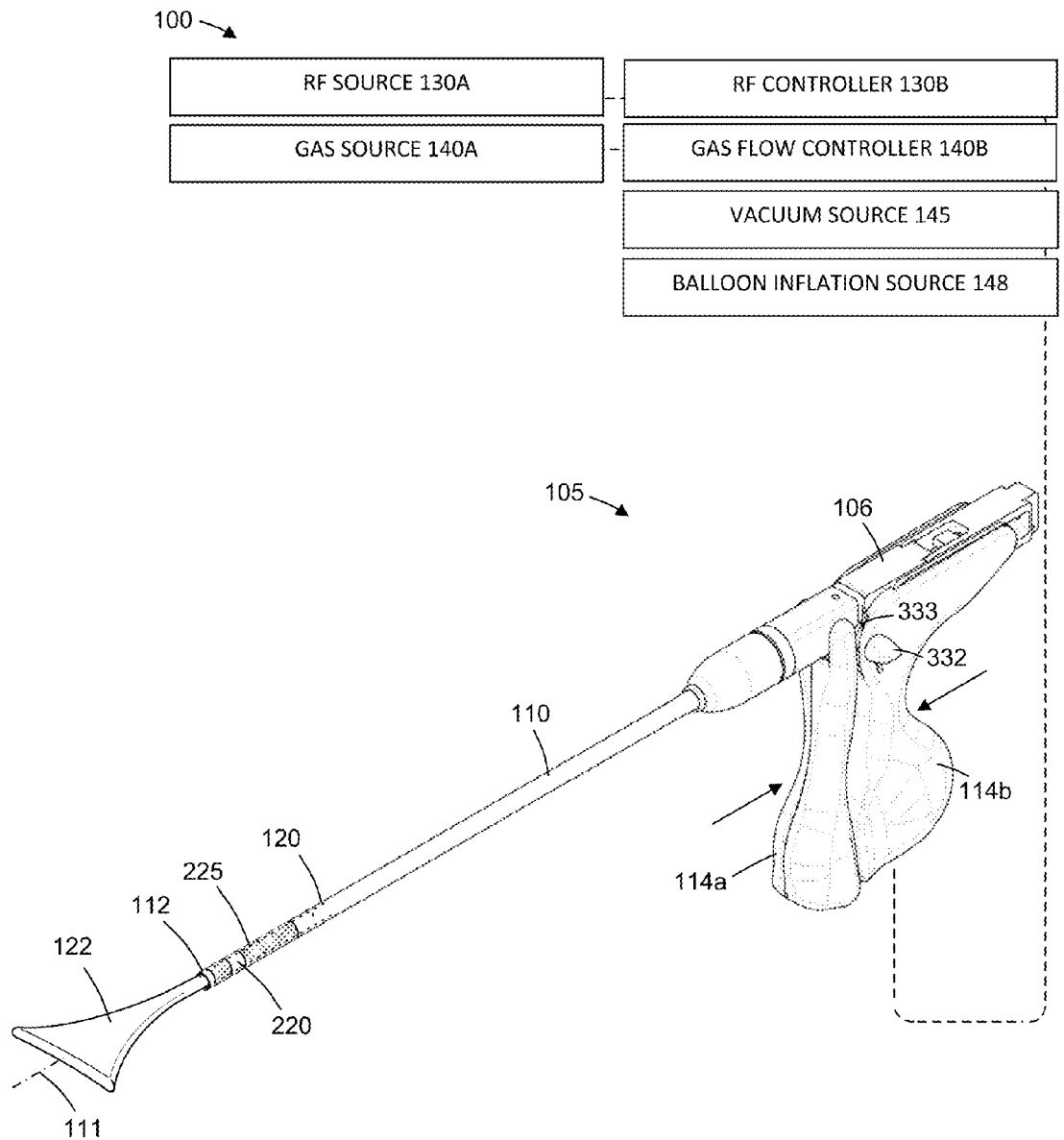
FIG. 2 is a view of the hand-held electrosurgical device of FIG. 1 with a deployed, expanded thin-wall dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-wall plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
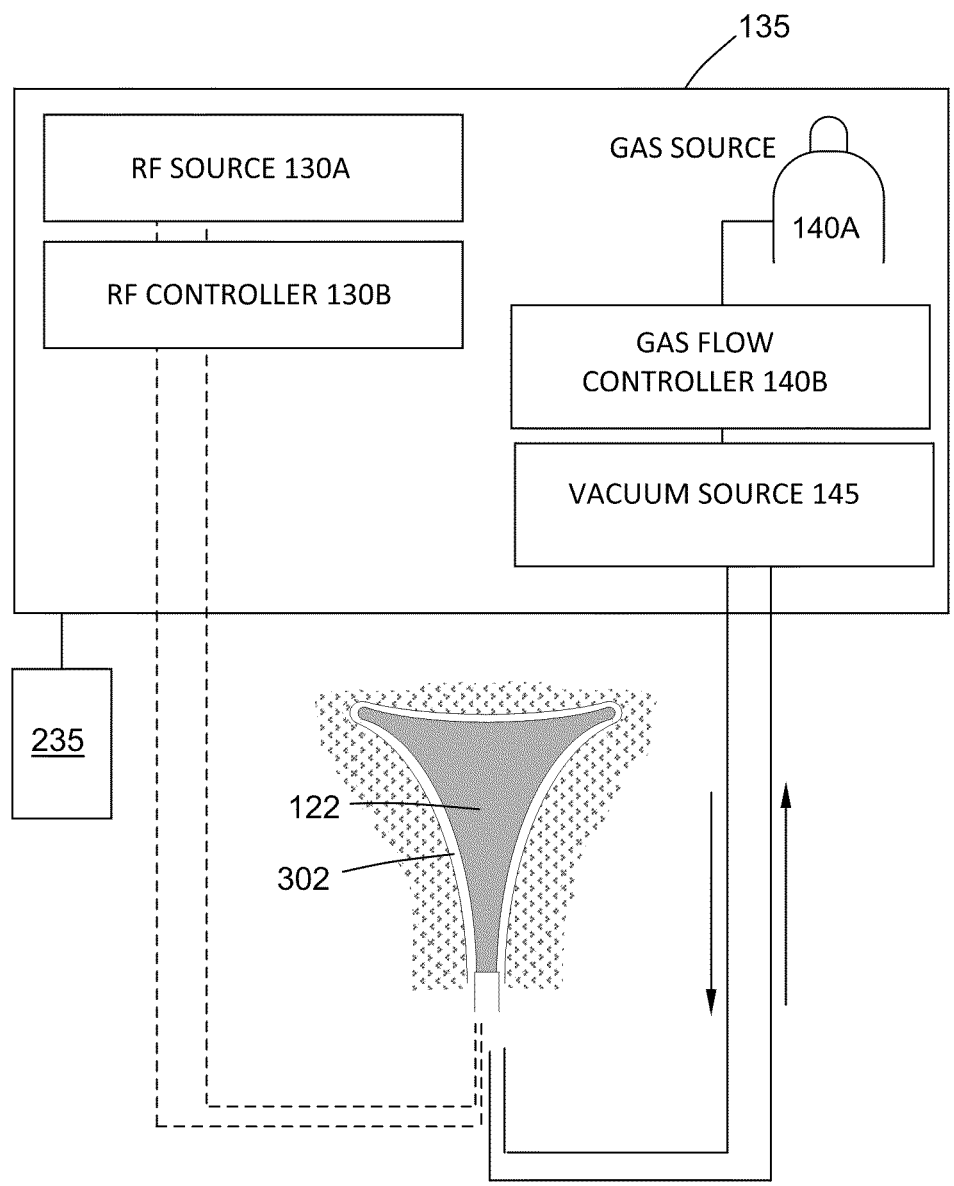
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-wall member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-wall material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-wall structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162a and 162b of spring elements 158a, 158b are fixed (e.g., by welds 164) to the distal end 165 of sleeve member 115. The proximal ends 166a and 166b of spring elements 160a, 160b are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176a and 176b of spring elements 158a, 158b are welded to distal ends 178a and 178b of spring elements 160a and 160b to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show that a plurality of gas inflow ports 188 can be provided along a length of in sleeve 170 in chamber 152, as well as a port 190 in the distal end of sleeve 170 and bumper element 185. The sectional view of FIG. 7 also shows the gas flow passageways within the interior of introducer sleeve 110.

Figure 5:
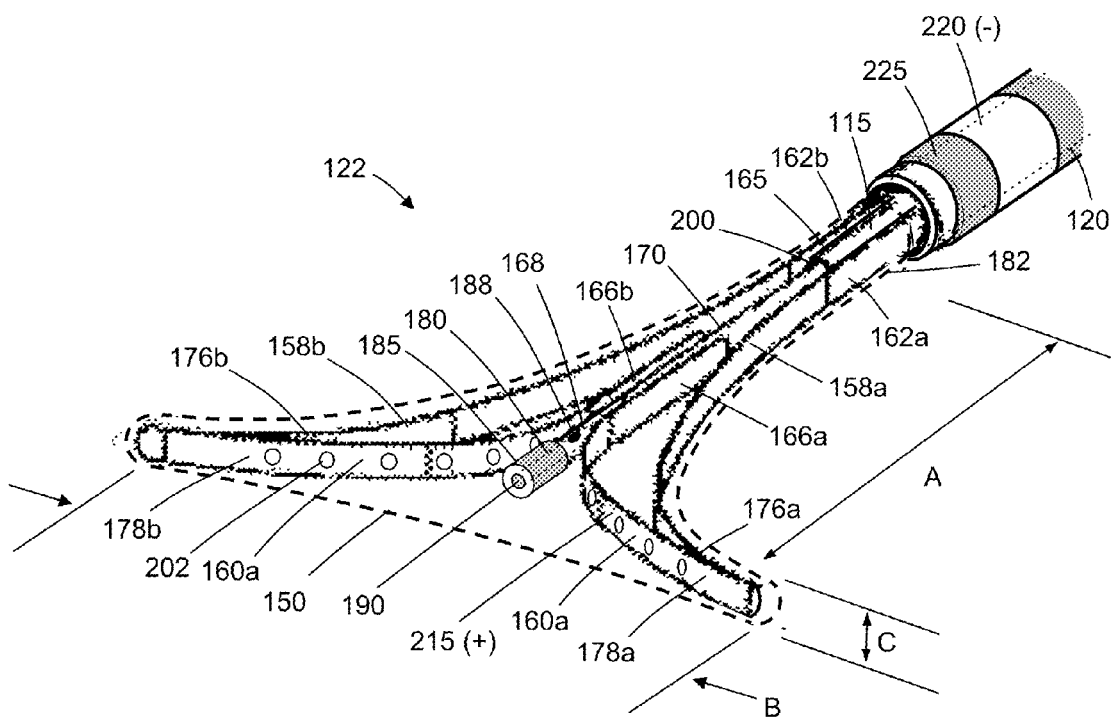
FIG. 5 is an enlarged perspective view of the expanded thin-wall dielectric structure, showing an expandable-collapsible frame with the thin dielectric wall in phantom view.
Figure 6:
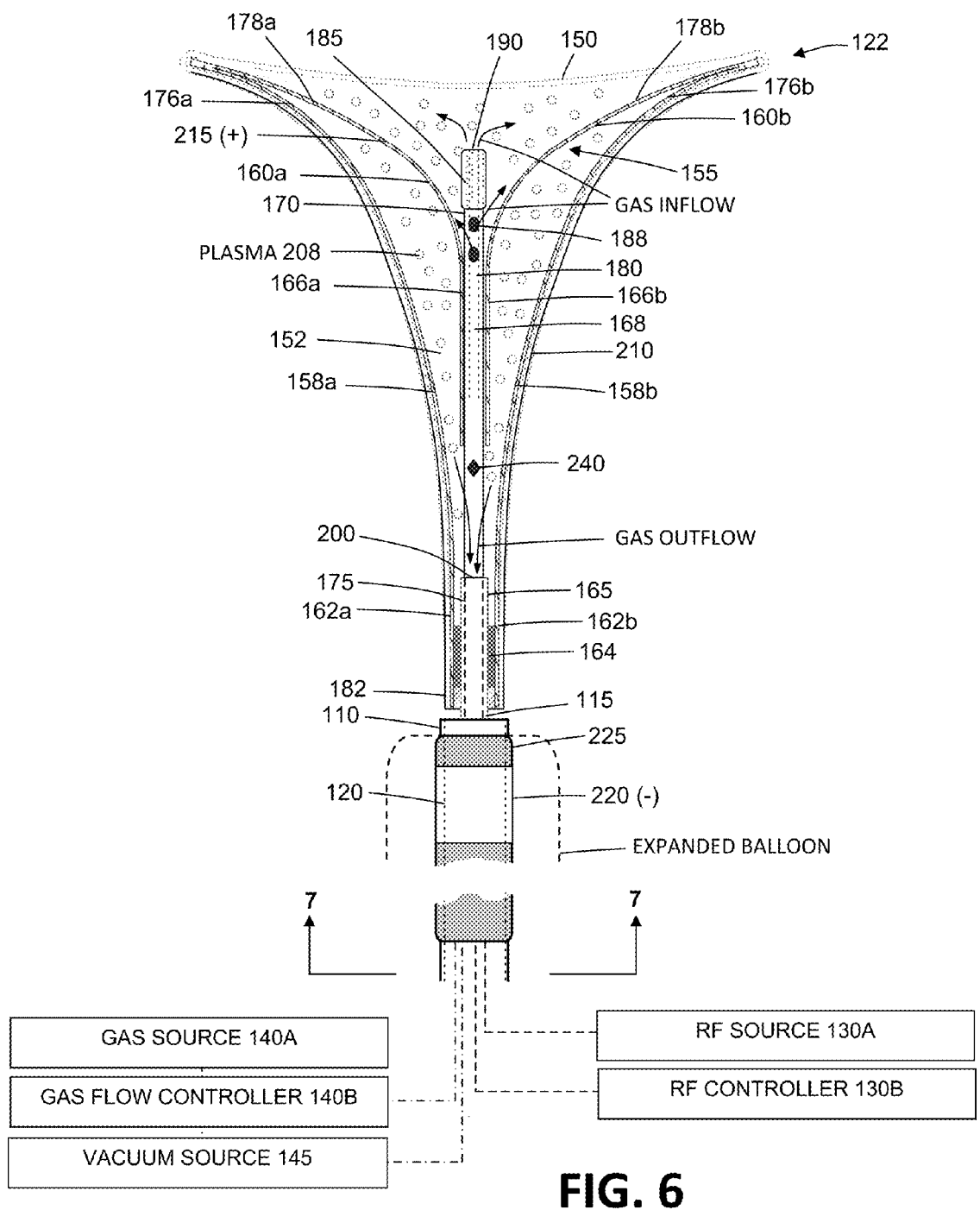
FIG. 6 is a partial sectional view of the expanded thin-wall dielectric structure of FIG. 5 showing (i) translatable members of the expandable-collapsible frame a that move the structure between collapsed and (ii) gas inflow and outflow lumens.
Figure 7:
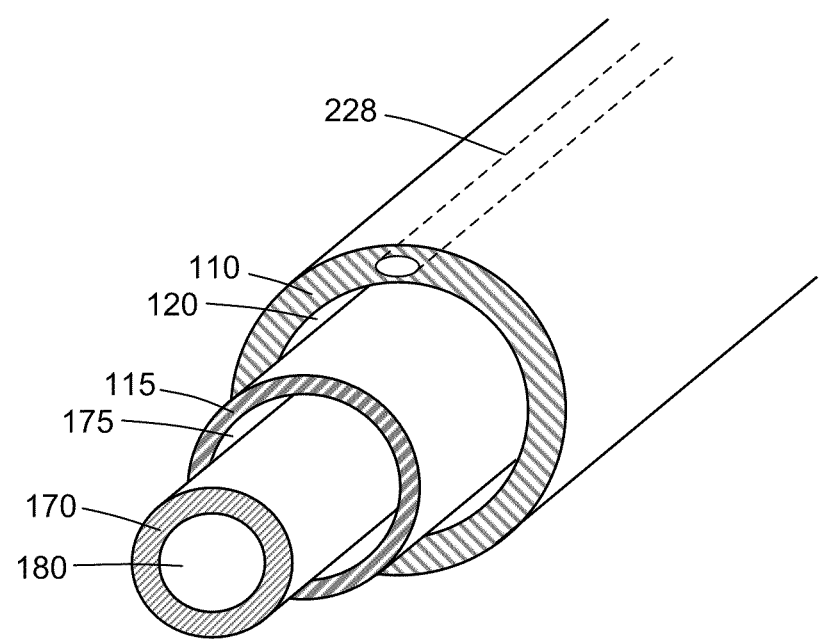
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114a and 114b, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-wall structure 150 can be from 1 to 4 mm as determined by the dimensions of spring elements 158a, 158b, 160a and 160b of frame assembly 155. It should be appreciated that the frame assembly 155 can comprise round wire elements, flat spring elements, of any suitable metal or polymer that can provide opening forces to move thin-wall structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-wall structure 150 that is formed of a dielectric material such as silicone that permits capacitive coupling of current to engaged tissue while the frame assembly 155 provides structural support to position the thin-wall structure 150 against tissue. Further, gas inflows into the interior chamber 152 of the thin-wall structure can assist in supporting the dielectric wall so as to contact endometrial tissue. The dielectric thin-wall structure 150 can be free from fixation to the frame assembly 155, or can be bonded to an outward-facing portion or portions of frame elements 158a and 158b. The proximal end 182 of thin-wall structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2).

As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-wall dielectric structure 150. In FIGS. 5 and 6, it can be seen that gas outflows communicate with vacuum source 145 through open end 200 of bore 175 in sleeve 115. Referring to FIG. 5, it can be seen that frame elements 158a and 158b are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-wall structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-wall dielectric structure 150 to endometrial tissue in contact with the wall 210. The electrosurgical methods of capacitively coupling RF current across a plasma 208 and dielectric wall 210 are described in U.S. patent application Ser. No. 12/541,043; filed Aug. 13, 2009 and U.S. application Ser. No. 12/541,050, referenced above. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-wall dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-wall dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-wall compliant balloon having a length of about 1 cm to 6 cm that can be expanded to seal the cervical canal. The balloon 225 can be inflated with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touchscreen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
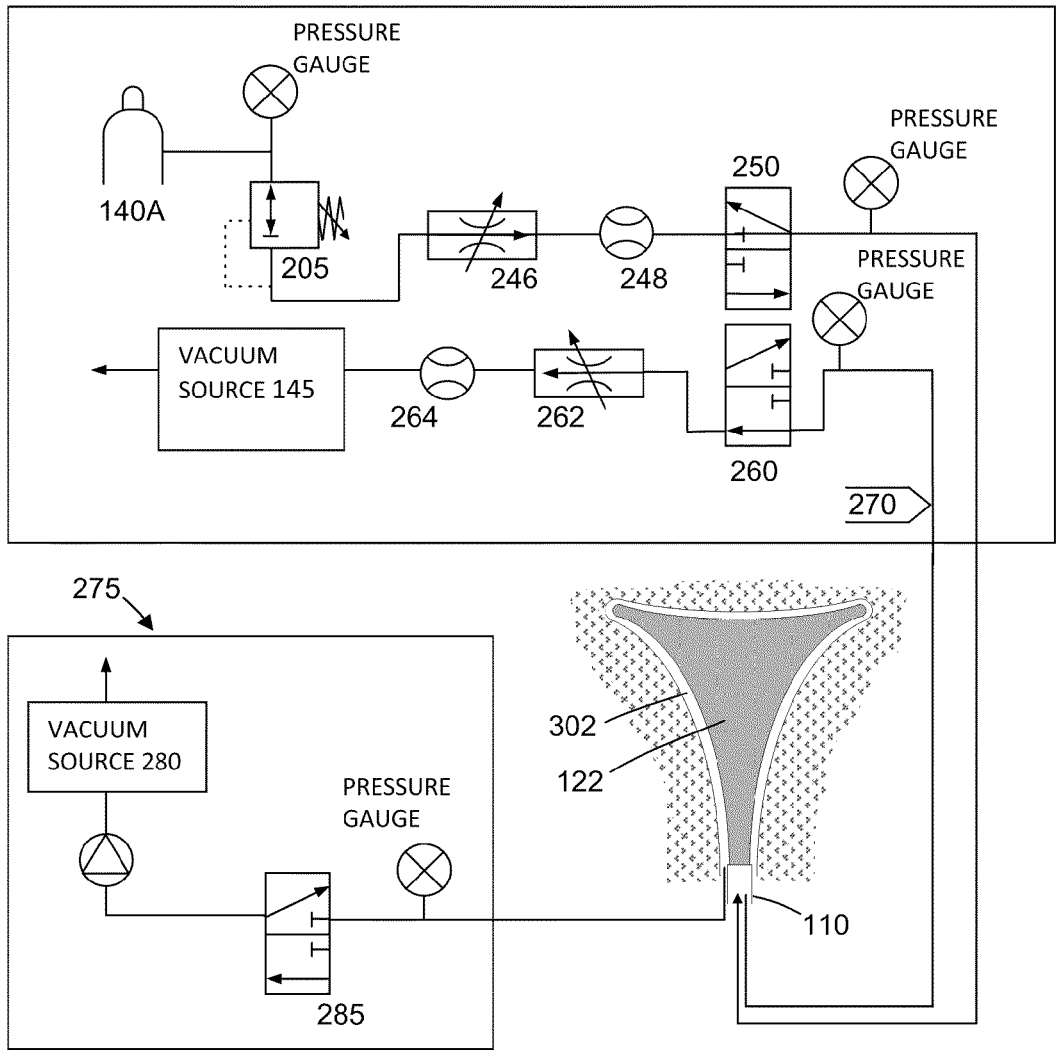
FIG. 4 s a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flowmeter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided.

FIGS. 8A-8D schematically illustrate a method of the invention wherein (i) the thin-wall dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
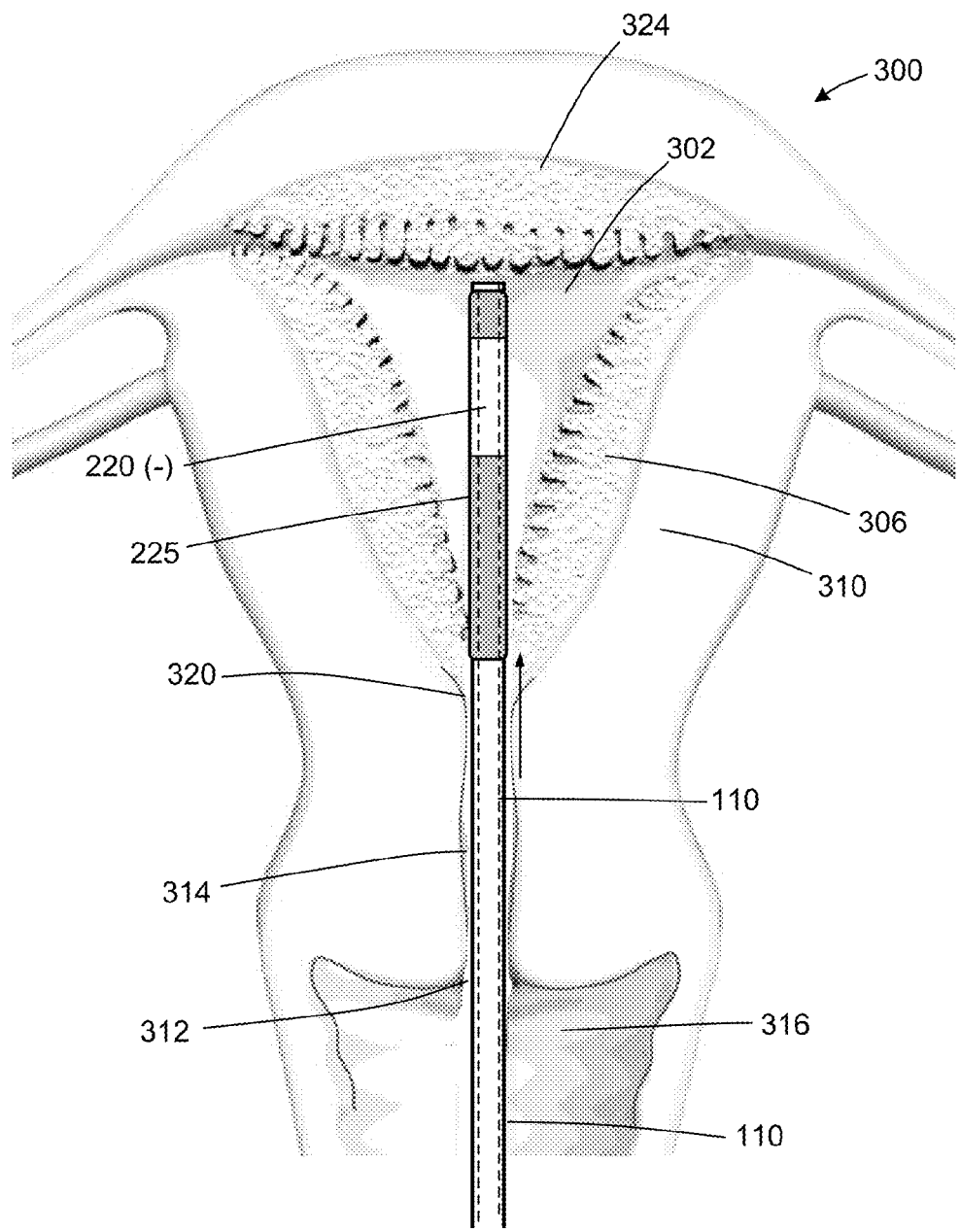
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
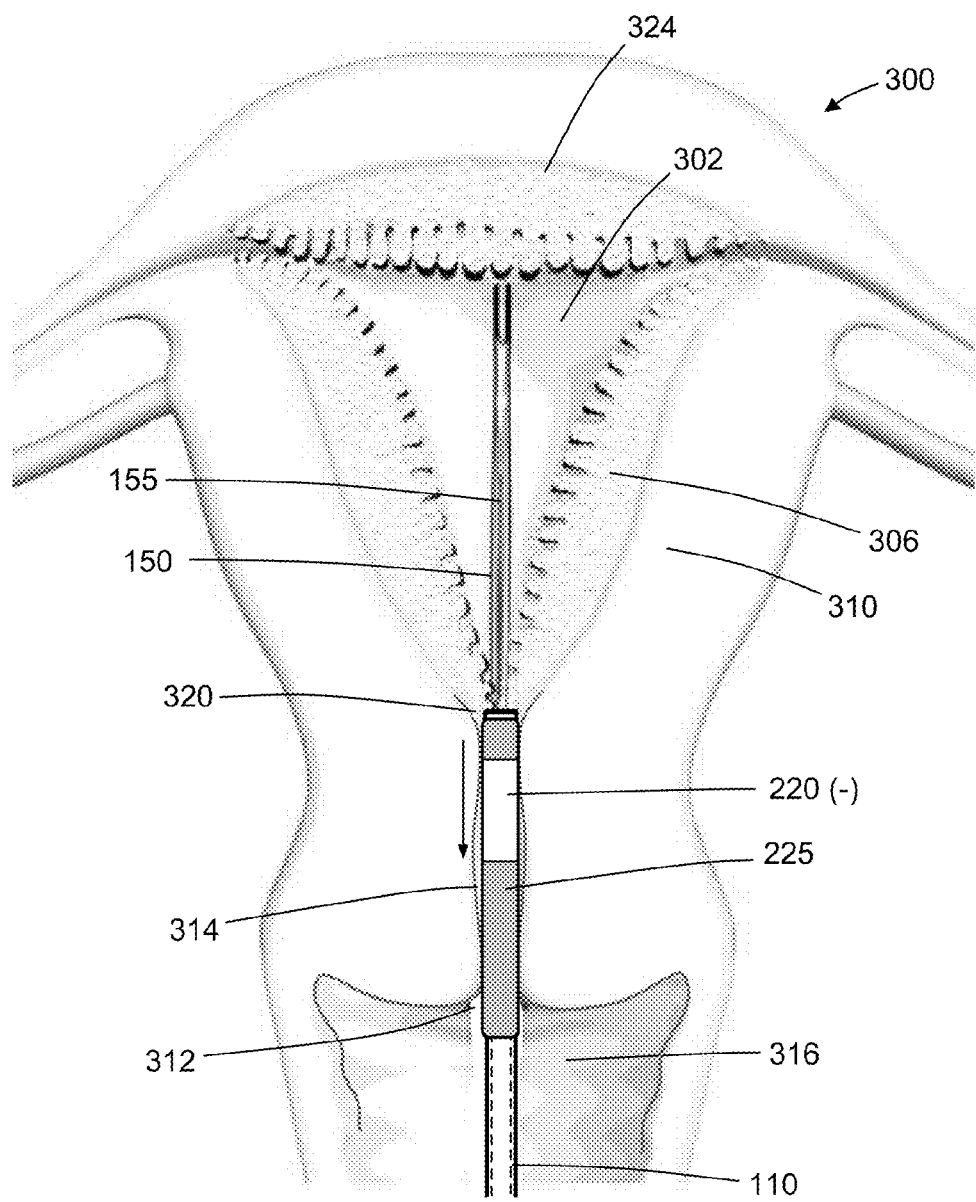
FIG. 8B is a schematic view of a subsequent step of retracting the introducer sleeve to expose a collapsed thin-wall dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-wall structure 150 within the uterine cavity 302. The sleeve 110 can be retracted to expose a selected axial length of thin-wall dielectric structure 150, which can be determined by markings 330 on sleeve 115 (see FIG. 1) which indicate the axial travel of sleeve 115 relative to sleeve 170 and thus directly related to the length of deployed thin-wall structure 150. FIG. 2 depicts the handle portions 114a and 114b fully approximated thus deploying the thin-wall structure to its maximum length.

Figure 8C:
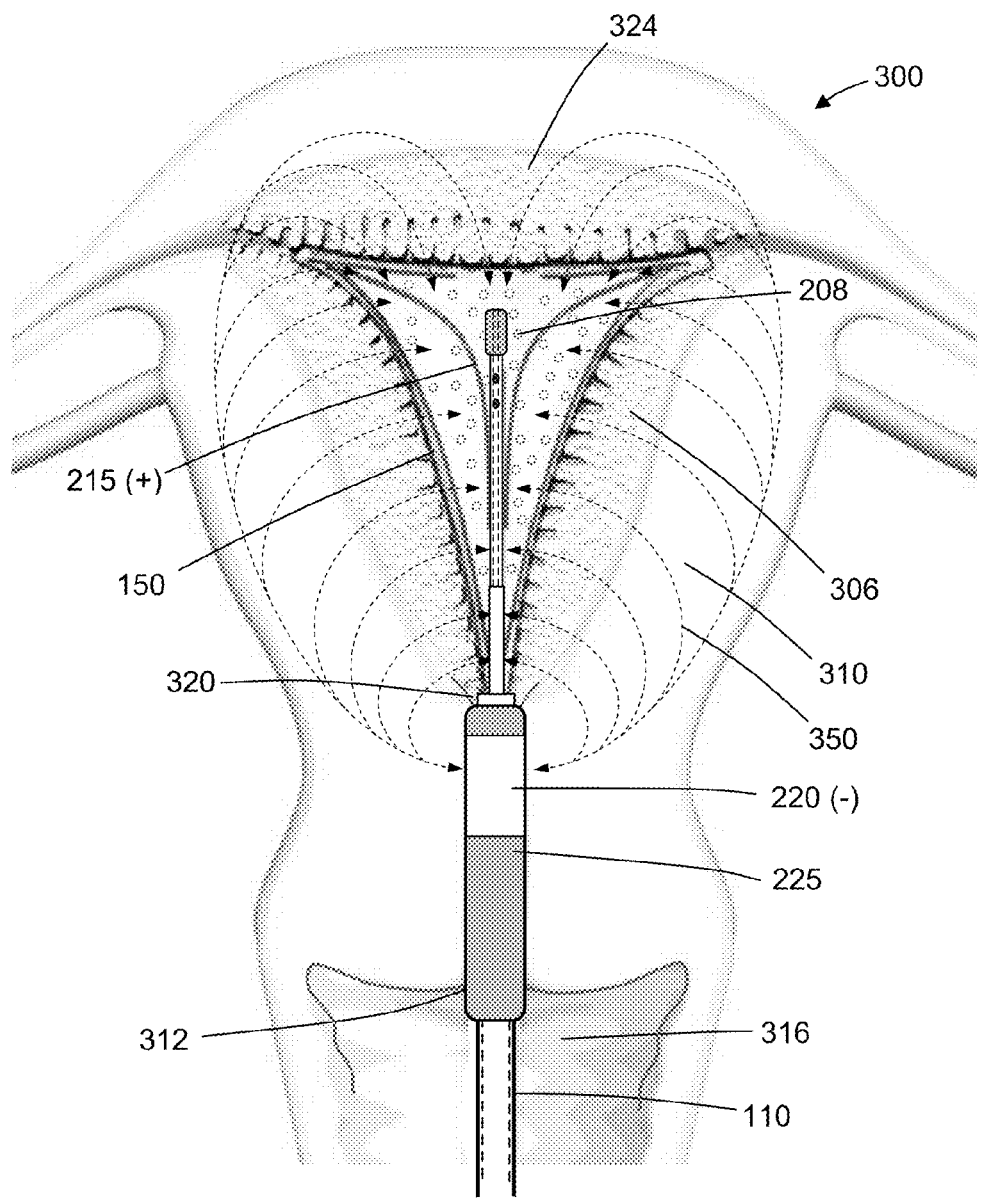
FIG. 8C is a schematic view of subsequent steps of the method, including, (i) actuating the internal frame to move the a collapsed thin-wall dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-wall dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-wall structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-wall structure 150 can be deployed in the uterine cavity with a selected length, and the spring force of the elements of frame 155 will open the structure 150 to a selected triangular shape to contact or engage the endometrium 306. In one embodiment, the expandable thin-wall structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-wall dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-wall structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-wall dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-wall structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of three mm to six mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
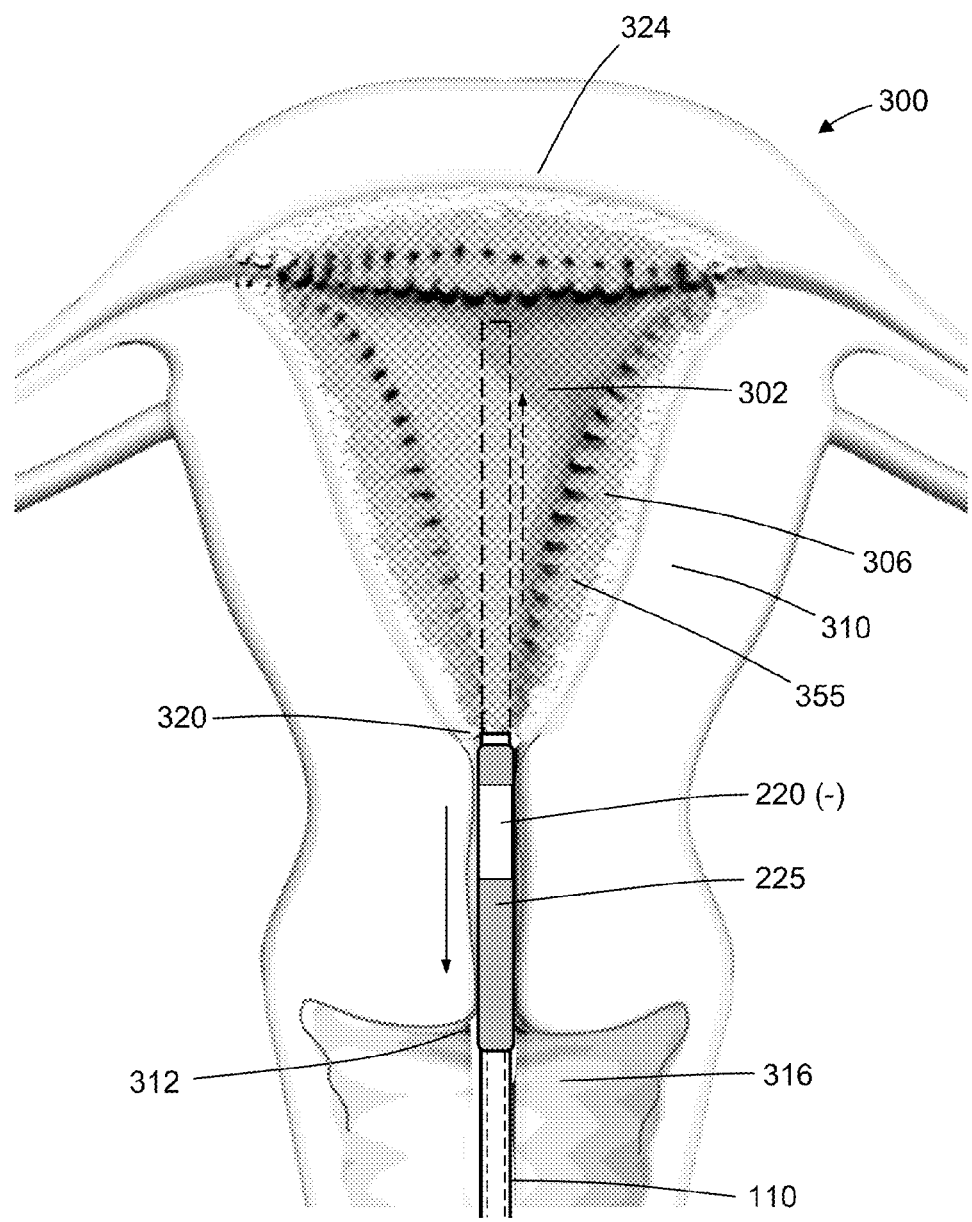
FIG. 8D is a schematic view of a subsequent steps of the method, including: (i) advancing the introducer sleeve over the thin-wall dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-wall structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
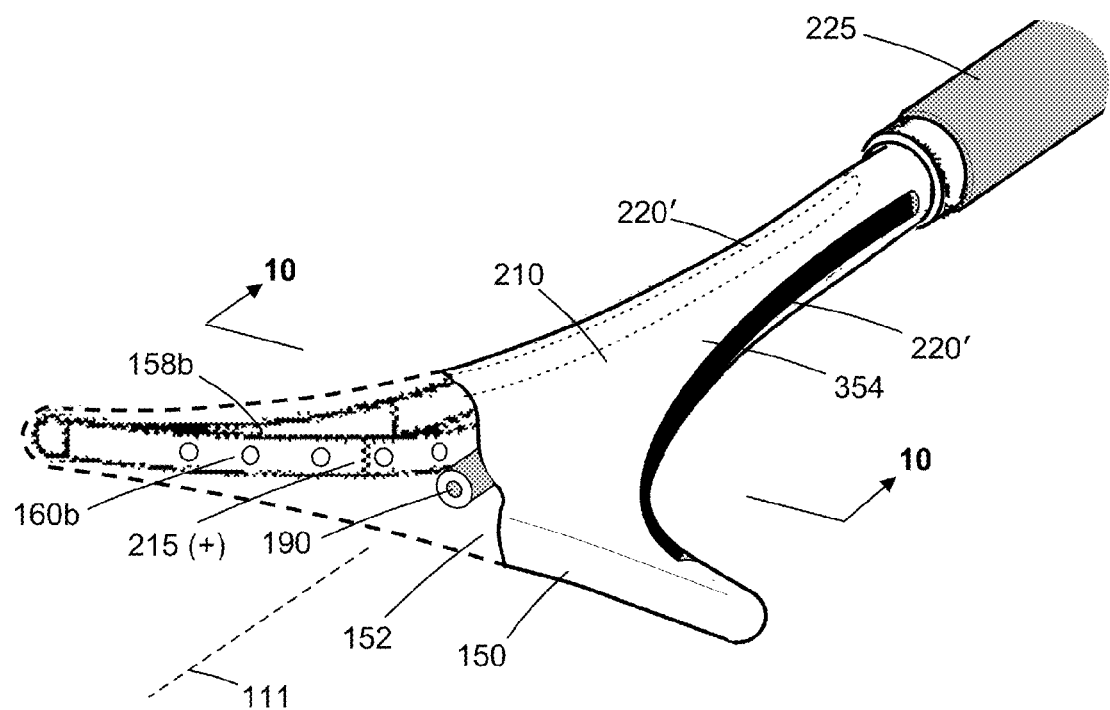
FIG. 9 is a cut-away perspective view of an alternative expanded thin-wall dielectric structure similar to that of FIGS. 5 and 6 show an alternative electrode configuration.
Figure 10:
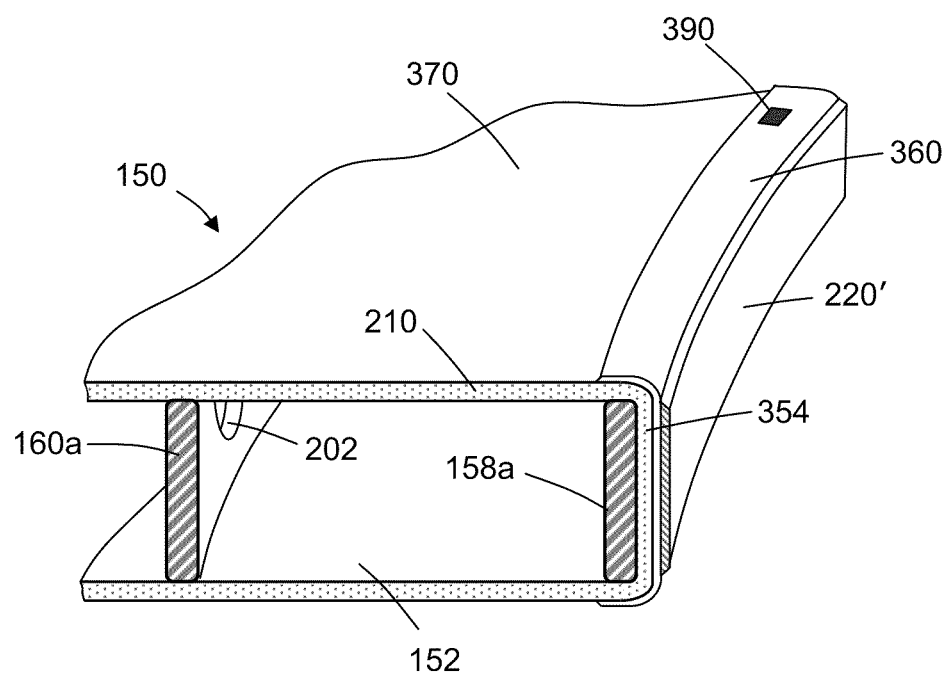
FIG. 10 is an enlarged cut-away view of a portion of the expanded thin-wall dielectric structure of FIG. 9 showing the electrode configuration.

Now turning to FIGS. 9 and 10, an alternate working end 122 with thin-wall dielectric structure 150 is shown. In this embodiment, the thin-wall dielectric structure 150 is similar to that of FIGS. 5 and 6 except that the second polarity electrode 220' that is exterior of the internal chamber 152 is disposed on a surface portion 370 of the thin-wall dielectric structure 150. In this embodiment, the second polarity electrode 220' comprises a thin-film conductive material, such as gold, that is bonded to the exterior of thin-wall material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6 to modulate or terminate RF energy delivery or to modulate gas flows within the system.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:
1. A system for endometrial ablation comprising:
a thin dielectric wall at least partially surrounding an interior chamber and having a shape for positioning in a uterine cavity;
a gas source configured to deliver a non-conductive gas into the interior chamber;
a first polarity electrode exposed to the interior chamber;
a second polarity electrode external to the interior chamber for contacting patient tissue; and
a radiofrequency energy source coupled to the first and second polarity electrodes configured to provide a voltage sufficient to convert the non-conductive gas to a plasma and to capacitively couple current across the dielectric wall to endometrial tissue.

2. The system of claim 1, wherein the dielectric wall has a triangular configuration for contacting endometrial tissue about the uterine cavity.

3. The system of claim 1, wherein the dielectric wall comprises a distensible material.

4. The system of claim 1, wherein the dielectric wall comprises a non-distensible material.

5. The system of claim 1, wherein the dielectric wall comprises a silicone.

6. The system of claim 1, wherein the dielectric wall has a thickness in the range from 0.005 inches to 0.020 inches.

7. The system of claim 1, wherein the dielectric wall is capable of being shifted between contracted and expanded shapes.

8. The system of claim 1, further comprising a support structure in the interior chamber capable of being shifted between contracted and expanded shapes.

9. The system of claim 8, wherein the support structure comprises spring elements to bias the dielectric wall toward an expanded shape.

10. The system of claim 8, wherein the first polarity electrode comprises at least a portion of the support structure.

11. The system of claim 8, further comprising an elongated introducer connected to the dielectric wall and support structure.

12. The system of claim 11, wherein the second polarity electrode is carried by the introducer.

13. The system of claim 10, wherein the second polarity electrode is carried on an exterior surface of the dielectric wall.

14. The system of claim 11, further comprising at least two lumens in the introducer communicating with the interior chamber for providing a gas inflow from the gas source and a gas outflow out of the interior chamber, respectively.

15. The system of claim 14, wherein the gas source comprises a remote gas source coupled to one of the two lumens in the introducer for providing the gas inflow into the interior chamber.

16. The system of claim 15, further comprising a controller operatively coupled to the gas source for controlling gas inflow.

17. The system of claim 14, wherein the gas source comprises a gas source coupled to one of the two lumens in the introducer for providing a gas inflow into the interior chamber.

18. The system of claim 17, further comprising a controller operatively coupled to the vacuum source for controlling gas outflow.

19. The system of claim 1, wherein the interior chamber has a volume in the range from 1 ml to 10 ml.

20. The system of claim 1, wherein the radiofrequency energy source is configured to deliver in the range from 500V to 2500V.

21. An endometrial ablation device comprising:
   an elongated introducer having a handle end and a working end;
   an expandable dielectric wall carried at the working end, defining an interior chamber, and configured, when expanded, to contact endometrial tissue;
   a gas source for flowing a neutral gas into the interior chamber; and
   first and second polarity electrodes disposed internal and external to the interior chamber, respectively;
   wherein, when the dielectric wall is expanded to contact endometrial tissue and the interior chamber is filled with the neutral gas, application of a radiofrequency voltage across the first and second polarity electrodes causes a plasma to form in the neutral gas and capacitively couples current across the dielectric wall to ablate endometrial tissue.

22. The endometrial ablation device of claim 21, wherein the first polarity electrode comprises a portion of a support structure for supporting the dielectric wall in an expanded shape.

23. The endometrial ablation device of claim 21, wherein the second polarity electrode comprises an exterior surface portion of the dielectric wall.

24. The endometrial ablation device of claim 21, wherein the second polarity electrode comprises a portion of the introducer.

25. The endometrial ablation device of claim 21, wherein the gas source is configured to circulate gas through the interior chamber.

26. The endometrial ablation device of claim 21, wherein the gas source is configured to provide a flow of neutral gas into the interior chamber.

27. The endometrial ablation device of claim 26, wherein the a flow rate of the neutral gas into the interior chamber is within the range from 0.05 ml/sec to 50 ml/sec.

28. The endometrial ablation device of claim 21, wherein the gas source is configured to permit the flow of at least one of the neutral gas and the plasma out of the interior chamber.

29. The endometrial ablation device of claim 21, further comprising an expandable frame for expanding the dielectric wall.

30. The endometrial ablation device of claim 29, wherein the frame supports the dielectric wall.

31. The endometrial ablation device of claim 29, wherein the expandable frame comprises the first polarity electrode.

32. The endometrial ablation device of claim 29, wherein the second polarity electrode is carried on an exterior surface of the dielectric wall.

33. The endometrial ablation device of claim 21, wherein the dielectric wall has a triangular configuration for contacting endometrial tissue about the uterine cavity.

34. The endometrial ablation device of claim 21, wherein the dielectric wall comprises a distensible material.

35. The endometrial ablation device of claim 21, wherein the dielectric wall comprises a non-distensible material.

36. The endometrial ablation device of claim 21, wherein the dielectric wall comprises a silicone.

37. The endometrial ablation device of claim 21, wherein the dielectric wall has a thickness in the range from 0.005 inches to 0.020 inches.

38. The endometrial ablation device of claim 21, wherein the dielectric wall is capable of contracted and expanded shapes.

39. The endometrial ablation device of claim 21, further comprising an expandable member mounted to the introducer for sealing the cervical canal of the patient.

40. The endometrial ablation device of claim 39, wherein the expandable member comprises a balloon.

* * * * *